United States Patent [19]

Hardwick et al.

[11] Patent Number: 5,336,760

[45] Date of Patent: Aug. 9, 1994

[54] METHOD AND USEFUL APPARATUS FOR PREPARING PHARMACEUTICAL COMPOSITIONS

[75] Inventors: R. Alan Hardwick, El Toro; Alan K. Smith, Mission Viejo; William C. Lake, Laguna Niguel; Dennis E. Chenoweth, Laguna Hills, all of Calif.

[73] Assignee: Baxter International Inc., Deerfield, Ill.

[21] Appl. No.: 838,711

[22] PCT Filed: Sep. 14, 1990

[86] PCT No.: PCT/US90/05228

§ 371 Date: Mar. 12, 1992

§ 102(e) Date: Mar. 12, 1992

Related U.S. Application Data

[63] Continuation of Ser. No. 407,487, Sep. 14, 1989, abandoned.

[51] Int. Cl.$^5$ .......................... B03C 1/32; C07K 3/18; C07K 17/14; G01N 33/553

[52] U.S. Cl. ..................................... 530/413; 209/39; 209/214; 209/223.2; 210/222; 210/695; 422/270; 436/526; 530/811

[58] Field of Search ................ 436/526; 530/413, 811; 422/270; 210/222, 695; 209/39, 214, 223.2

[56] References Cited

U.S. PATENT DOCUMENTS

| | | | |
|---|---|---|---|
| 3,905,865 | 9/1975 | McAleer et al. | 435/240.23 |
| 3,970,518 | 7/1976 | Giaever | 195/1.5 |
| 4,219,411 | 8/1980 | Yen et al. | 209/213 |
| 4,628,037 | 12/1986 | Chagnon et al. | 436/526 |
| 4,710,472 | 12/1987 | Saur et al. | 435/287 |
| 4,740,371 | 4/1988 | St. Remy et al. | 424/85 |
| 4,846,786 | 7/1989 | Freed et al. | 530/413 |
| 4,855,045 | 8/1989 | Reed | 210/223 |
| 4,861,705 | 8/1989 | Margel | 435/2 |
| 4,904,391 | 2/1990 | Freeman | 210/695 |

FOREIGN PATENT DOCUMENTS

| | | |
|---|---|---|
| 0150735 | 8/1985 | European Pat. Off. |
| 0152746 | 8/1985 | European Pat. Off. |
| 0253455 | 1/1988 | European Pat. Off. |
| 0317279 | 5/1989 | European Pat. Off. |
| 2449892 | 2/1980 | France |
| WO89/04373 | 5/1989 | PCT Int'l Appl. |
| WO91/02083 | 2/1991 | PCT Int'l Appl. |
| 626043 | 8/1978 | U.S.S.R. ................. 210/222 |
| 1366218 | 1/1988 | U.S.S.R. ............... 209/232.2 |

OTHER PUBLICATIONS

"Removal of Neuroblastoma Cells from Bone Marrow with Monoclonal Antibodies Conjugated to Magnetic Microspheres" by J. G. Treleaven, J. Ugelstadt, T. Philips, F. M. Gibson, A. Rembaum, G. D. Caine, and J. T. Kemshead, The Lancet, (Jan. 14, 1984), pp. 70–73.

Primary Examiner—Jeffrey E. Russel
Attorney, Agent, or Firm—Michael Schiffer; Janice Guthrie

[57] ABSTRACT

The invention provides an apparatus and method for the preparation of a pharmaceutical composition comprising a complex of an antigen component and the corresponding antibody component in a pharmacologically acceptable carrier. The apparatus comprises a housing chamber for containing paramagnetic particles and a platform against which the housing chamber is releasably retained. The platform contains one or more magnets located adjacent to the housing chamber when the housing chamber is positioned on the platform. The platform is secured to a support which allows the platform, and thus the housing chamber, to be rotated between a vertical and a horizontal position. The method involves supplying a quantity of paramagnetic particles bearing the antigen component to the housing chamber, introducing into the housing chamber a physiological fluid which contains the antibody component, mixing the paramagnetic particles and the physiological fluid to form an antigen component and antibody component complex on the paramagnetic beads, removing the physiological fluid from the housing chamber, and eluting the antigen component and antibody component complex from the paramagnetic beads in a pharmaceutically acceptable eluting solution.

23 Claims, 2 Drawing Sheets

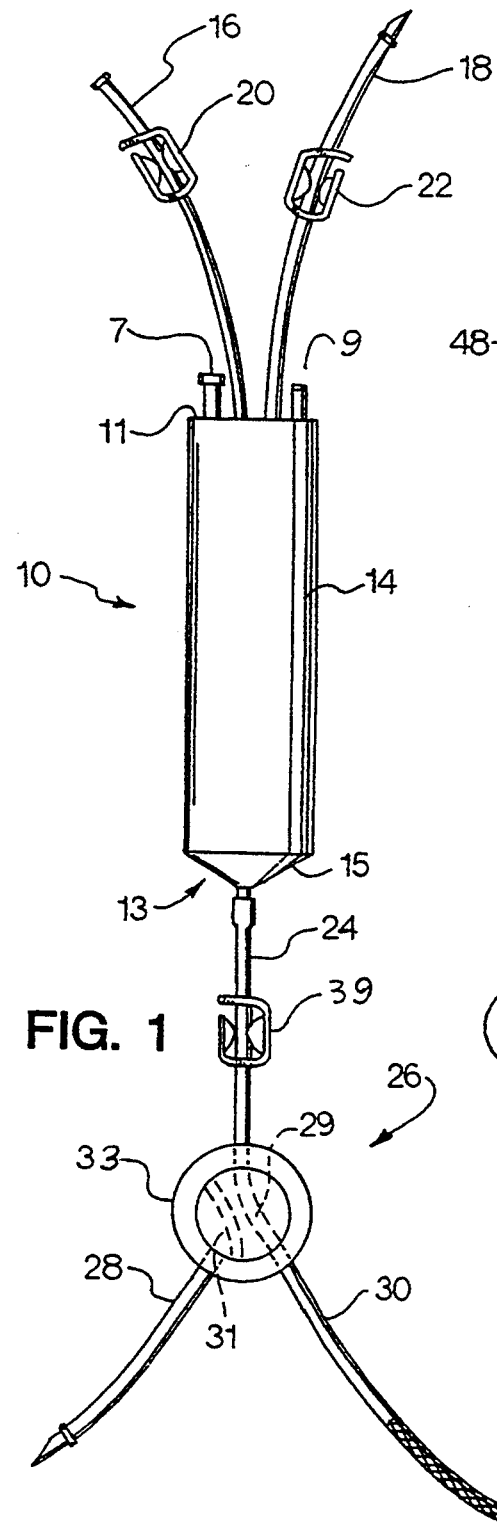
FIG. 1
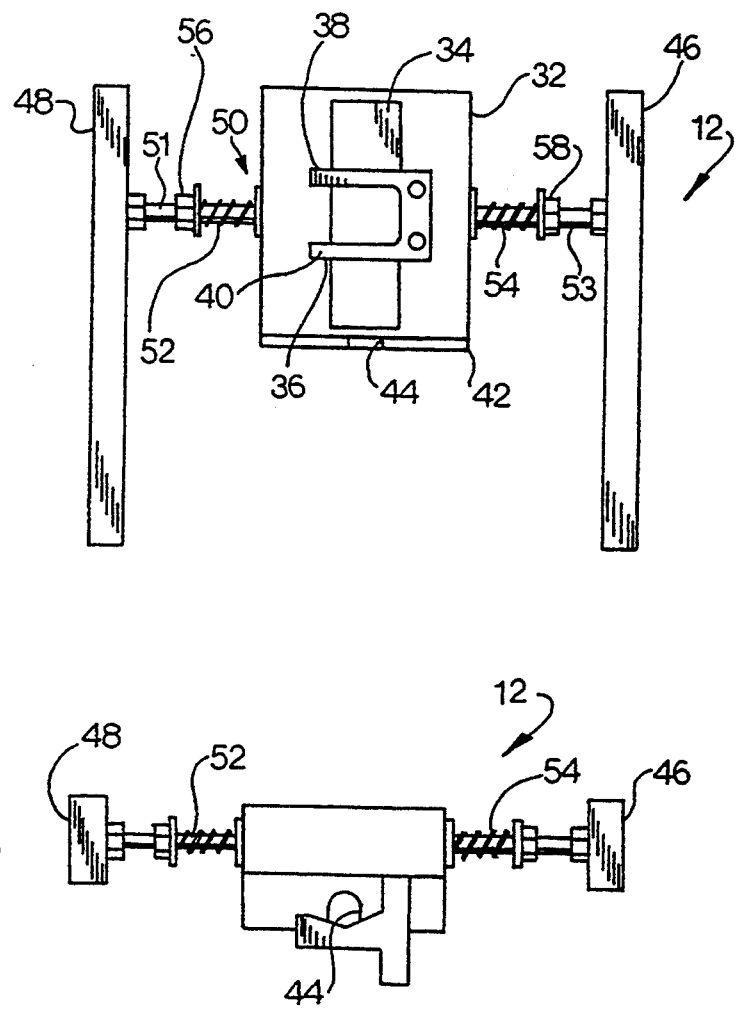
FIG. 2a
FIG. 2b

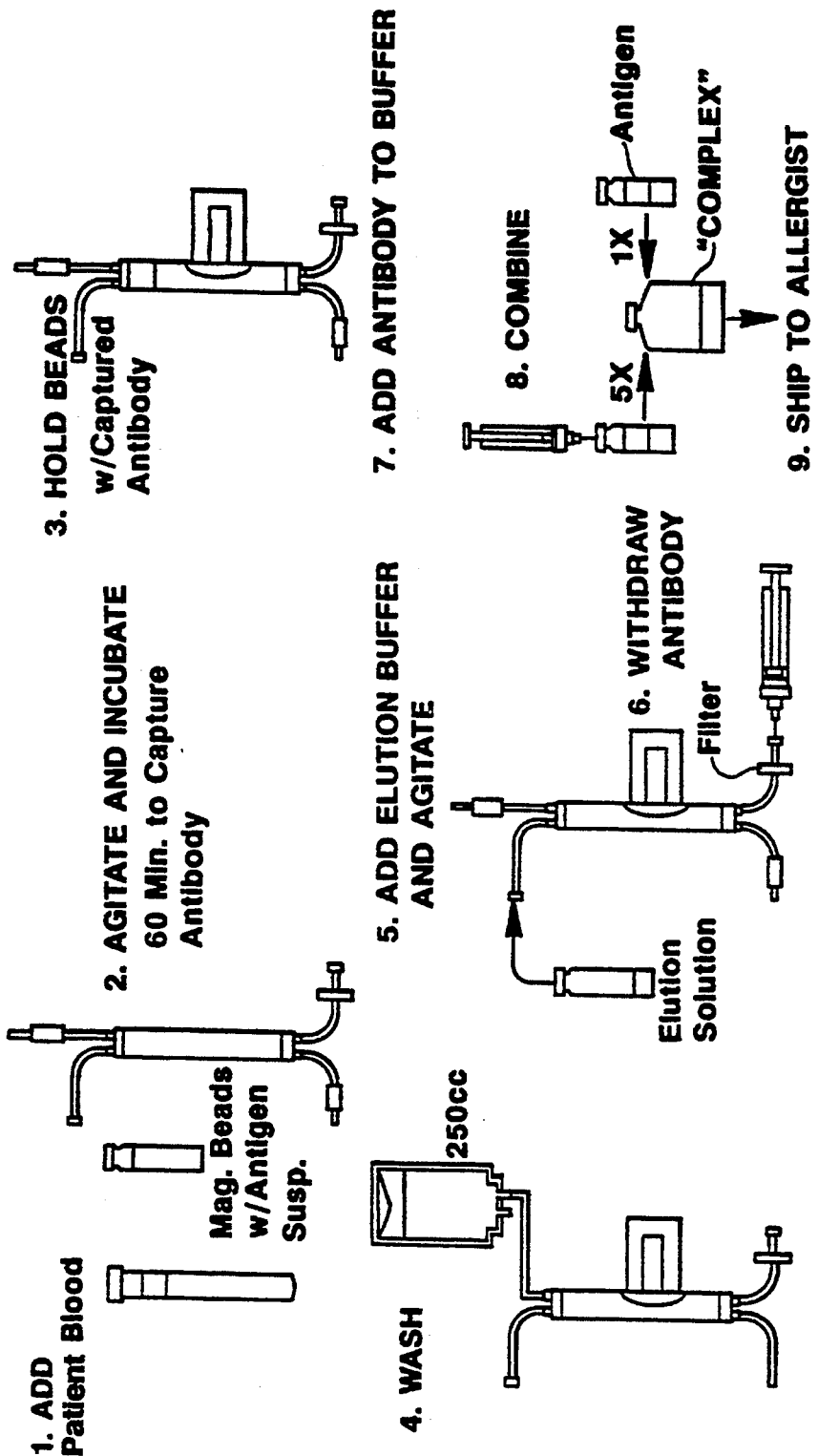

METHOD AND USEFUL APPARATUS FOR PREPARING PHARMACEUTICAL COMPOSITIONS

This is a continuation of U.S. Ser. No. 07/407,487 filed Sep. 14, 1989, now abandoned.

BACKGROUND OF THE INVENTION

The present invention is related to devices and methods of using the same, to prepare pharmaceutical compositions comprising a complex of an antigen component and the corresponding antibody or inhibitor component in a pharmacologically acceptable carrier. Specifically, the invention concerns a device and method of using the same, of preparing a pharmaceutical composition by selectively isolating an antibody type component from a physiological fluid, such as blood, plasma or other bodily fluid in a pharmacologically acceptable carrier to which the antigen type compound may be added.

Pharmaceutical compositions containing antibody/antigen complexes have been suggested for numerous medical applications. For example, U.S. Pat. No. 4,740,371, issued to St. Remy et al on Apr. 26, 1988, disclosed a complex useful for treating allergies. This complex includes the specific allergen that causes the allergic reaction, and the corresponding antibody for that allergen. While the antibodies may be derived from either the patient's or a donor's physiological fluids, the preferred antibody is usually derived from the patient's own physiological fluids. The injection of this complex reduces, and even eliminates, a patient's allergic reaction to the specific allergen, while not possessing the side effects accompanying conventional allergy treatments.

Another antibody/antigen complex is taught in EP 426913, published May 15, 1991. This application discloses a complex composed of factor VIII and an antibody termed factor VIII inhibitor. This complex is used to treat hemophiliacs who have become refractory to the injection of factor VIII. These individuals produce a factor VIII inhibitor antibody which binds with, and renders factor VIII inactive. Thus factor VIII functions as the antigen, while the anti-factor VIII functions as the antibody. It was demonstrated that the injection of the factor VIII antigen/inhibitor complex reduces some patient's refractortness to factor VIII injections.

The antigen/antibody complexes taught in St. Remy et al and the pending application preferably use the antibody from the patient's own physiological fluids. This is significant not only because it eliminates any potential reaction to an antibody prepared from a nonidentical donor, but more importantly, autologous antibodies are most effective for induction of the therapy itself. The presently available methods, as taught by St. Remy et al and the referenced application, of extracting the antibodies requires painstaking chemical isolation of the antibody from the patient's bodily fluid, such as blood. For example, St. Remy et al discloses isolating the desired antibodies IgG, IgM, IgA, IgE, and IgD by a complex series of steps involving precipitation, dialysis, concentration, chromatography and immunoadsorption.

Thus while pharmaceutical compositions containing antigen/antibody complexes may be beneficial in the treatment of certain diseases and conditions, the methods of isolating the desired antibody are complex and time consuming. It is thus desirable to provide a mechanism to readily prepare pharmaceutical antibody/antigen complexes.

Recent advances in separation technology have presented the opportunity of isolating a specific target population, e.g. cells, proteins, or antibodies without the need of tedious and extensive chemical separation techniques. For example, various workers have suggested capturing specific target populations by using filters bearing immunoreactive groups. Immunoreactive groups are those to which the desired antibody will selectively bind, typically the antigen. These techniques include filters prepared from fibers bearing immunoreactive groups, U.S. Pat. No. 3,843,324, issued on Oct. 22, 1974; columns bearing immunoreactive group, U.S. Pat. No. 4,252,653, issued on Feb. 24, 1981; and filter candles bearing immunoreactive groups, U.S. Pat. No. 4,648,974, issued Mar. 10, 1987.

Another recently developed technique for isolating target populations, i.e. antibodies, selected proteins and cells, from a physiological fluid utilizes paramagnetic beads or particles coated with an immunoreactive compound or agent selective for the desired target population. Examples of such particles or beads are disclosed in U.S. Pat. Nos. 4,230,685, issued Oct. 28, 1980; 4,554,088, issued Nov. 19, 1985; and 4,628,037, issued Dec. 9, 1986. The use of such particles in the separation of taught in publications, "Removal of Neuroblastoma Cells From Bone Marrow with Monoclonal Antibodies Conjugated to Magnetic Microspheres", by J. G. Treleaven, J. Ugelstad, T. Philips, F. M. Gibson, A. Rembaum, G. D. Caines and J. T. Kemshead, *The Lancet*, Jan. 14, 1984, pages 70–73, and "Immunomagnetic removal of B-lymphoma cells from human bone marrow: a procedure for clinical use", by G. Kvalheim, O. Sorensen, O. Fodstad, S. Funderud, S. Kiesel, B. Dorken, K. Nustad, E. Jakobsen, O. Ugelstad and A, Pihl, *Bone Marrow Transplantation*, (1988), volume 3, pages 31–41.

Other references which disclose devices and methods of isolating specific target populations are U.S. Pat. Nos. 3,970,518, and 4,018,886 both issued to Giaever on Jul. 20, 1976 and Apr. 19, 1977, respectively, 4,219,411, issued to Yen et al on Aug. 26, 1980 and 4,710,472, issued to Saur et al on Dec. 1, 1987. Both Yen et al and Saur et al disclose intricate devices for mixing a physiological fluid with Immunoreactive paramagnetic particles. These immunoreactive paramagnetic particles are coated with an agent specific for the target population, that is, will selectively bind to the target population cellular members or chemical species. These paramagnetic particles are subsequently captured by a magnetic field while removing the fluid.

The Giaever patents disclose devices and methods of isolating the select population of cells from a physiological fluid using the immunoreactive paramagnetic particles. The immunoreactive paramagnetic particles and the physiological fluid are mixed in a vessel. Once the immunoreactive agents, i.e. antibody layer, has bonded with the target population cells or chemical species, the particles are separated from the fluid by activating a magnetic coil to capture and immobilize the particles and opening a valve to release the fluid from the vessel. The immunoreactive paramagnetic particles are then transferred to another vessel containing a cleaving agent. This cleaving agent promotes the release of the selected target population from the coated paramagnetic particles.

The above discussed procedures and apparatus allow for the separation of a target population, whether cells, proteins or antibodies, from a physiological fluid. The procedures for which these methods are used are typically those in which it is desired to remove this target population from the physiological fluid prior to returning the fluid to the patient. For example, the above procedure is useful for removing infected or tumor cells from a specific tissue, e.g. bone marrow. The major drawback to the described procedures and apparatus is the complexity of the procedure or apparatus used, or the inability of thoroughly separating the target population from the remainder of the physiological fluid. That is, the disclosed procedures and apparatus were not as concerned with the complete removal of most of the physiological fluid since the primary focus is the removal of the target population. Thus there remains the risk of some contamination of the target population with extraneous cells or compounds from the fluid.

Further, such procedures and apparatus have the drawback of requiring multiple containers for performing the isolation, as described in Giaever et al, or require specific knowledge of procedures to insure prevention of contamination of the final product. It thus remains desirable to provide for a method and apparatus which would simplify the handling and isolation of a target population, and specifically an antibody, for the purpose of easily, and safely preparing a pharmaceutical composition.

SUMMARY OF THE INVENTION

The present invention overcomes the above described disadvantages by providing a method, and useful apparatus for the preparation of pharmaceutical compositions comprising a complex of an antigen component and the corresponding antibody component in a pharmacologically acceptable carrier.

The process of the invention is carried out by isolating the selected antigen component/antibody component complex in a pharmaceutically acceptable carrier in a chamber.

Generally the process of the invention involves preparing a pharmaceutical composition of a specific target antibody component population in a pharmaceutically acceptable carrier from a physiological fluid in a chamber having at least one inlet and outlet comprising:
bringing the physiological fluid into contact with a solid phase support bearing an antigen component selective for the target antibody component population;
removing the physiological fluid from the chamber;
washing the chamber with an acceptable wash fluid;
draining the washing fluid from the chamber;
supplying a pharmaceutically acceptable eluting solution to the chamber; and
removing the eluting solution from the chamber.

Additionally, the invention relates to a disposable, aseptic single use fluid processing pathway that can be used to obtain a predetermined amount of an antigen-specific antibody from a patient's physiological fluid to treat allergy or autoimmune disease by immunization with autologous or homologous antigen:antibody immune complexes.

Additionally, this invention relates to a method to obtain a predetermined amount of allergen-specific antibody from physiological fluid to conduct a course of immunotherapy treatment for an allergic reaction to that specific allergen comprising:

adding a sufficient amount of a physiological fluid and a sufficient number of allergen coated particles to bind a predetermined amount of allergen-specific antibody to an aseptic separation chamber;
incubating said fluid and the allergen coated particles for a sufficient period of time to bind the allergen-specific antibody to the allergen coated particles in the chamber;
means to separate the allergen-specific antibody bound to the allergen coated particles from unbound fluid;
means to separate said allergen-specific antibody bound to said allergen coated particles from unbound fluid;
removing the unbound fluid from the chamber;
washing the allergen coated particles to remove non-specifically adsorbed materials in the chamber;
adding an amount of a physiologically acceptable elution solution to elute the allergen-specific antibody from the allergen coated particles, but less than an amount of the elution solution to require concentration of the recovered allergen-specific antibody;
incubating the allergen-specific antibody bound to the allergen coated particles with the elution solution for a sufficient period of time to elute the allergen-specific antibody from the allergen coated particle;
means to separate the allergen-specific antibody from the allergen coated particles in the chamber, to obtain a predetermined amount of allergen-specific antibody;
adding an amount of a physiologically acceptable neutralizing buffer to the allergen-specific antibody to obtain a solution having a physiologically acceptable pH, but less than an amount of the neutralizing solution to require concentration of the allergen-specific antibody, In accordance with a preferred embodiment of the invention the solid phase support are paramagnetic particles bearing the antigen component'selective for the antibody component target population. Specifically, the method of the invention involves preparing a pharmaceutical composition by isolating a target antibody component population from a physiological fluid in a pharmaceutically acceptable carrier, which isolation is performed in a chamber which is at least partially magnetically permeable and includes an inlet and outlet comprising:
mixing the physiological fluid and immunoreactive paramagnetic particles bearing an antigen component selective for the target antibody component population;
capturing the immunoreactive paramagnetic particles in magnetic field to hold the paramagnetic particles in the chamber;
draining the fluid from the chamber;
adding a washing fluid to the chamber;
removing the washing fluid from the chamber;
supplying a pharmaceutically acceptable eluting solution to the chamber; and
removing the eluting solution from the chamber.

The invention is also directed to a device for selectively isolating a target antibody component population from a physiological fluid in accordance with the described method. This device includes a housing defining a chamber, which includes at least one inlet and outlet for gaining entrance to the chamber. The housing is preferably formed at least partially from a magnetically permeable material. The device further includes a platform against which the housing is rested and releaseably retained. This platform may be positioned in either a substantially horizontal or vertical position. The platform may also include one or more magnets located adjacent to housing when positioned on the platform. In accordance with a preferred embodiment, the platform is secured to a support which allows the platform, and thus the housing to be rotated between a substantially vertical to substantially horizontal position.

Additionally, the invention is also directed to a kit comprising reagents and a disposable aseptic separation device to recover eluted antibody, said kit being used to form autologous or homologous antigen:antibody immune complexes to treat allergy or autoimmune disease.

BRIEF DESCRIPTION OF THE DRAWINGS

The present invention may be better understood and the advantages will become apparent to those skilled in the art by reference to the accompanying drawings, wherein like reference numerals refer to like elements in the several figures, and wherein:

FIG. 1 is a prospective illustration of a container assembly in accordance with an embodiment of the invention suitable for performing the method of the invention;

FIG. 2A is a front view of a support assembly in accordance with an embodiment of the invention; and FIG. 2B is a top view of FIG. 2A.

FIG. 3 is a schematic diagram of the present invention in the kit format, to form antigen allergen-antibody immune complexes to treat allergy or autoimmune disease,

DESCRIPTION OF THE PREFERRED EMBODIMENTS

The present invention is directed to a method and useful apparatus, for preparing a pharmaceutical composition directly from a physiological fluid, e.g. blood or plasma. The pharmaceutical compositions prepared in accordance with the method and apparatus of the invention are those compositions useful for treating ailments caused by the reaction of the body to a specific antigen component.

For the purpose of this invention "antigen component" shall be defined generally as any compound or molecule having a chemical site which is recognized and bound to by an antibody component (as herein defined). Examples of antigen components are those compounds or molecules which react with immunoglobulin molecules. Antigen component shall include antigens in general, and also any other naturally occurring or foreign compound which invokes an immunological response from the body. Examples of specific antigen components in accordance with the invention are proteins, carbohydrates, hormones, allergens, and factor VIII, when the administration of factor VIII to hemophiliacs causes a refractory response.

For the purpose of this invention "antibody component" shall be generally defined as any compound or molecule which reacts with a recognized chemical site of an antigen component, and in particular an immunoglobulin which the body produces in response to an antigen component. Examples of antibody components include those immunoglobulins produced in response to viruses, allergens and factor VIII inhibitor, antibiotics, chemicals, or any substance where this response occurs. In this regard, antibody component shall include those immunoglobulins produced by the body in response to compounds.

Generally, the method of the invention involves selectively isolating a desired target antibody component population from a patient's physiological fluid using a solid phase support to which selective antigen components have been affixed. This solid phase support will typically be particles or beads prepared with a coating or layer of an antigen component selective for the desired antibody component which may be admixed with the physiological fluid. Although, it may be possible to use the chamber walls as the solid phase support. It is generally desireable to immobilize as much antigen on the particle or bead as possible to facilitate the capture of the greatest amount of antibody. The antibody components bind to the antigen component forming an antigen component/antibody component complex. The fluid and beads are then separated, with any unbound materials, e.g. cells, proteins or other compounds washed away from the particles. The beads can be separated by magnetic separation if they are paramagnetic or by filtration if they are not magnetic. The particles are then contacted with an elution solution which either causes the disassociation of the antibody component from the antigen component, or cleaves the antigen component/antibody component complex from the particles or beads. This elution solution is collected and used to prepare the pharmaceutical composition.

Preferred particles are immunoreactive paramagnetic particles or beads. The types of paramagnetic particles useful for the practice of the invention are typically polymeric spherical particles having diameters from about 3 to about 8 microns. These particles are formed with small amounts of magnetite, which causes the particles to be captured by a magnetic field. However, these types of particles do not retain any magnetism after removing the field. Generally paramagnetic particles are those having a magnetic susceptibility per unit volume from about $1 \times 10^{-3}$ to about $1 \times 10^{-2}$ cgs units.

The paramagnetic particles useful for practicing the invention should provide for an adequate antigen component binding surface capacity, while possessing a low non-specific binding characteristic. That is, the particles should be prepared from a material which ensures an adequate capacity for retaining antigen component, while also being a material which possesses limited reactivity with compounds or materials other than the desired antigen component. Examples of suitable paramagnetic particles are disclosed in many of the above referenced patents, with a preferred paramagnetic particle being that sold under the identification number M450 by the Dynal Company of Great Neck, N.Y. Additionally, paramagnetic Sepharose ® (Pharmacia Inc.) beads may be employed.

The precise type of paramagnetic particle used in the practice of the invention is not critical and will not be described any further herein, so long as the paramagnetic particles possess a desired capacity for the specific antigen component and are characterized by having a low binding characteristic for compounds, cells or other materials other than the desired antigen component.

As stated, the particles are prepared with an antigen component coating selective for the desired antibody component. The resulting particles are generally referred to herein as immunoreactive paramagnetic particles. The antigen component coating includes that antigen component to which the desired antibody component normally binds to form a complex. Examples of antigen components useful for the practice of the invention include those compounds and substances generally known as allergens, i.e. compounds which produce an allergic response. Another example of a useful antigen component is factor VIII. As described in EP 426913, published May 15, 1991, mentioned above, factor VIII functions as the antigen component for factor VIII inhibitor, which is an antibody component. For a detailed description of the treatment of allergies and factor VIII refractortness see St. Remy et al and the stated co-pending application, both of which are generally incorporated herein by reference.

In accordance with the method of the invention, the selective isolation of the desired antibody component is performed by bringing a physiological fluid containing the specific antibody component into contact with the immunoreactive particles, and preferably with immunoreactive paramagnetic particles.

The physiological fluid may be obtained directly from the patient or from multiple donors. Specifically, the physiological fluid may be blood, plasma, lymphatic fluid, cerebrospinal fluid, or derivatives thereof. The physiological fluid should include a sufficient quantity of the desired antibody component. For example, physiological fluid taken for the purposes of providing a composition to treat allergic responses should be taken from patients or donors that have been sensitized to that specific allergen either as a result of natural exposure or active immunization. Similarly, hemophiliacs who suffer from the clinical consequences associated with the production of factor VIII inhibitor will normally have a measurable level of such inhibitor present in their blood.

The physiological fluid may have been previously subjected to a technique used to grossly separate various constituents, for example centrifugation techniques used to separate larger blood cells from lighter plasma and proteins, including the desired antibody component. This gross separation may enhance the method of the invention.

In accordance with the preferred embodiment using immunoreactive paramagnetic particles, these particles are admixed with the physiological fluid, typically in a container. When the container is employed as part of a single use kit to treat allergy or autoimmune disease by immunization with autologous antigen:antibody immune complexes, the volume of the container may range from about 0.25 mL to 500 mL, but preferably 60 mL of fluid. If homologous antibodies are used more than 500 mL of physiological fluid may be required. "Homologous" means derived from the same species e.g. Gamma Guard ® (Baxter Healthcare Corporation, Hyland Division). The container is one which is at least partially magnetically permeable, i.e. at least a portion of the container is non-metallic. The container is then positioned within a magnetic field to capture and draw the immunoreactive paramagnetic particles towards a side of container. The use of multiple magnets positioned around the container to generate a strong field may result in the immunoreactive paramagnetic particles being drawn to more than one container side.

With the container maintained in the magnetic field, the physiological fluid is expelled. Typically, this is performed by opening a clamp or valve which releases the fluid through a line leading out from the container. A pump may be used to draw the fluid out of the container. The container may be positioned to place the outlet line in an orientation to allow for gravity flow of the fluid out of the container.

After the physiological fluid is expelled, an appropriate washing solution is added to the container to wash away any compounds which have non-specifically bound or adhered to the container walls or the paramagnetic particles. This typically requires adding saline to the container. The magnetic field is removed and the particles and saline admixed to ensure proper washing of the particle surfaces.

Subsequently, the container is again placed within the magnetic field to draw the paramagnetic particles against one or more sides, and the saline, or other suitable washing solution is expelled in a manner similar to that used to expel the physiological fluid. This washing step may be repeated as necessary. Thereafter, an eluting solution is added to the container. The eluting solution may either be washed over the particles maintained within the magnetic field, or the magnetic field may be removed and the particles suspended in the elution solution.

Eluting solutions suitable for the practice of the invention depend upon whether the antigen component-/antibody component complex is to be disassociated or cleaved entirely from the surface of the particles. In this regard the specific eluting solution used is dependent upon the bonding between the antigen component and antibody component or the chemical bond holding the antigen component to the particle surface. It should be noted that the eluting solution should not be of the type which would attack or damage the target antibody component.

Examples of eluting solutions useful for causing the disassociation of the antigen component/antibody component complex, that is the release of the antibody component from the antigen component, are disclosed in U.S. Pat. No. 4,740,371, issued to St. Remy et al and in U.S. Pat. No. 4,431,560, issued to Lake et al on Feb. 14, 1984, both of which disclosures pertaining to elution solutions are incorporated herein by reference. Specifically, elution solutions are disclosed in the Lake et al patent at column 2, line 18 through column 3, line 4. Other useful eluting solutions include acetic acid, citric acid or glycine. When it is desirable to cleave the antigen component/antibody component complex from the particle surface the covalent bond between the antigen component and the paramagnetic particles is broken by the use of a suitable technique. For example, the antigen component may be covalently bonded to the paramagnetic particles via tit sulfide bridges which are readily cleaved with a reducing agent.

The eluting solution should also be of the type which may be injected into a patient, that is a pharmaceutically acceptable solute, or of the type which is readily altered for injection into the patient. For example, when glycine is used, phosphate buffer may added in an appropriate amount to effect neutralization.

The precise type of eluting solution is not critical to the invention so long as it possesses the desired characteristics. Further, the volume of elution solution used should be substantially equivalent to the final volume desired for the pharmaceutical composition. In this regard, it would be desirable to neutralize the elution solution with a powder or equivalent material, e.g. buffer salts to minimize any increase in volume, otherwise the volume of the neutralizing agent must be taken into account when deciding upon the desired volume amount for the pharmaceutical composition. The volume of eluting solution will be significantly less than the amount of physiological and washing fluids used, typically on the order of 10 to 50 fold less, however, the volume could be smaller.

The incubation time of the eluting solution is from between 5 minutes to 24 hours to elute the antibody or antibody-antigen complex.

In the context of a single use kit to treat allergy or autoimmune disease, the volume of solutions added to the separation chamber or container is important. In particular, one of the features of this invention that allows the use of a kit is the ability to recover the desired antibody in a small volume, thus, eliminating the need to process the antibody further by way of concentration, dialysis, etc. In a full size device, elution volumes range from 0.1 to 5 mL, with the preferred range of 0.1 to 1.0 mL. The largest factor involved in minimizing the volume of elution buffer used is that if one uses too small an elution volume, a significant portion of the total elution buffer remains in the beads and thus a significant portion of the eluted antibody becomes entrapped in the beads and cannot be recovered. With this constraint in mind, another factor having an impact on the needed volume of elution buffer is the number of antigen or allergen beads used to bind the antibody. Another factor to be considered is that when employing too small an elution volume the yield of recovered antibody will suffer somewhat. The loss of yield must be balanced with the minimum quantity requirements for the recovered antibody. The optimal recovery of eluted anti-factor VIII antibody occurs while using 1 to 2 mL of elution buffer with $1-2 \times 10^9$ paramagnetic polystyrene (Dynal) beads in the 50 mL to 60 mL chamber.

The elution solution can be neutralized with a pharmaceutically acceptable neutralization solution such as phosphate or imidazole buffers. Similarly, as with the elution solutions, small volumes of neutralizing solution are required to facilitate packaging of this process as a kit. In particular, a small volume of a concentrated neutralization buffer can be employed so that neutralization does not result in a significant dilution of the eluted antibodies.

In the present invention, we have been able to accomplish neutralization of 1-2 mL of the 0.2 M glycine buffer, pH 2.5 with as little as 20-50 microliters of a concentrated neutralization buffer. Neutralizing buffers such as Tris, glycyl-glycine or borate may also be used. Additionally, it may be possible to choose a suitable neutralization buffer such as glycine or pyrophosphoric acid with a higher pKa which could allow the use of an even smaller volume of neturalization buffer. Additionally, a dry lyophilized neutralization buffer may be employed.

Critical elements that will dictate a suitable neutralization buffer will include such considerations as the "buffering capacity" of the buffer, the safety and toxicology characteristics of buffer, the solubility of the buffer salts, and the potential leaching of components of the contemplated glass vials in which the buffer will be stored in the kit form.

Typically, the pharmaceutical compositions prepared in accordance with the invention will require at least a minimum amount of the antigen component/antibody component complex in order to achieve the desired clinical result. This is independently established for treating each particular disease or syndrome. After the minimum requirement for the complex is established, the procedure can be standardized to achieve the desired concentration of the antigen component/antibody component complex in the pharmaceutical acceptable eluting solution. The method is particularly adaptable to allow individual practitioners to obtain and prepare the desired pharmaceutical composition with minimal effort and time from a patient's own physiological fluid. This thus allows for an immediate application of the desired pharmaceutical composition to the patient.

The first step in developing a procedure for a specific clinical need involves determining the minimum amount of the desired antigen component/antibody component complex. Once this is known, the necessary amount of antibody components is selected to be greater than or equal to the molar amount of the minimum amount of the antigen component population necessary to achieve the desired amount of the complex. Preferably the antibody component is used in a molar excess since additional antibody components will not interfere with the functioning of the composition, nor present harm to the patient, but will ensure adequate coverage of the antigen component.

It should be noted that under certain circumstances it may be desirable to provide for a molar excess of the antigen component rather than of the antibody component. For this purpose the following discussed procedures are followed in a similar manner except for the fact of allocating a molar excess of the antigen component.

The collection of the desired quantity of the antibody component is dependent upon the concentration of antibody components present in the particular physiological fluid being used, and the number of immunoreactive paramagnetic particles used in the practice of the invention. That is, once the minimum concentration of the antigen component/antibody component complex for therapeutic results is established, that volume of immunoreactive paramagnetic particles which possesses an adequate capacity for the binding of a sufficient quantity of antigen component to extract either a desired quantity or excess of the antibody component from a given quantity of the physiological fluid is used in the described method.

Two specific methodologies have been developed using the method of the invention for preparing specific antigen component/antibody component complexes in the treatment of allergic reactions and the treatment of factor VIII inhibitor. The first general methodology is disclosed in the incorporated herein patent issued to St. Remy et al on Apr. 26, 1988, U.S. Pat. No. 4,470,371. This patent teaches a composition useful for the treatment of allergic reactions. Basically, the disclosed composition is a complex of the specific antigen or allergen causing the allergic reaction, and the antibody specific for that allergen. In this regard all teachings and discussions concerning the administration of the allergen/antibody complex for the purpose of treating the allergic reaction are incorporated herein by reference, and specifically the teachings in column 3-6.

The major distinction between what is taught in St. Remy et al and the present invention concerns the method of isolating the antibody. This is specifically discussed at columns 7 and 8 under the heading 2, Antibody Purification. The purification procedure taught by St. Remy et al involves an intricate and time consuming purification method using concentration on and extraction techniques. The method of the invention allows for the purification of the antibody components in a simpler more concise manner with the use of the immunoreactive paramagnetic particles.

The concentration of the allergen/antibody complex necessary for achieving the desired therapeutic results discussed in St. Remy et al is specifically taught by St. Remy et al, and particularly at column 5, line 13, under the heading "2. Formation of the composition of the invention", and at Column 6, line 12, under the heading "Administration of the compositions", which is also incorporated herein by reference. A suitable quantity of the immunoreactive paramagnetic particles should be selected to provide for the desired quantity of antibody for complexing with allergen. In contrast to the above described method, a predetermined amount of antigen or allergen-specific antibody, for use in a kit, is an amount required for a course of treatment that does not require concentration or dialysis.

A second methodology is disclosed in the EP 426913, published May 15, 1991. This application teaches a composition useful for the treatment of the adverse reactions caused in some patients by factor VIII inhibitor. As discussed, some hemophiliacs develop an allergic type reaction to the administration of factor VIII. This reaction is caused by the presence of excessive quantities of factor VIII inhibitor. The methodology taught in this patent application involves the administration of a complex of the factor VIII inhibitor and factor VIII. In this regard all teachings and discussions concerning the administration of the factor VIII/factor VIII inhibitor complex for the purpose of treating the described condition are also incorporated herein by reference.

The above described method may be performed with any suitable device, e.g. the device disclosed in the EP 426913, published May 15, 1991. Further, when using immunoreactive particles which are non-paramagnetic, the device may include a filter for trapping the particles as the various fluids are being removed.

A preferred apparatus for performing the described method will now be discussed with reference to the several figures. The apparatus of the invention includes two parts, container assembly seen in FIG. 1 at 10, and support assembly seen in FIG. 2A and 2B at 12.

Container assembly 10 generally includes a separation chamber 14 having multiple inlets and outlets. This separation chamber 14 should be seal ed or in some manner closed off to external contamination. Container assembly 10 is designed to allow a user to perform the above described process entirely within the separation chamber 14. The separation chamber 14 is a generally elongated cylindrical body formed with two opposing ends 11 and 13. End 11 is provided with the various inlets, while end 13 includes at least one outlet and is formed to taper to this outlet, as seen generally as tapered portion 15.

To facilitate the introduction of the various fluids and immunoreactive paramagnetic particles, the separation chamber 14 is provided with fluid tubes 16 and 18. These fluid tubes 16 and 18 are used to introduce the physiological fluid into the separation chamber 14, via tube 16, and the saline or similar washing fluid, via tube 18.

The fluid tubes 16 and 18 extend out from end 11, and are either integrally formed with the separation chamber 14, or are mounted thereto in such a way to provide for a suitable seal. Clamps 20 and 22 are fitted about the fluid tubes 16 and 18, respectively. These clamps 20 and 22 are used to seal the respective fluid tubes 16 and 18 after the introduction of the specific fluid to prevent contamination. Typically, such clamps 20 and 22 may be Roberts, slide or roller clamps.

End 11 of container assembly 10 also includes a vent 7 and septum 9. Septum 9 is used to introduce the immunoreactive paramagnetic particles, not shown, and the elution fluid into the separation chamber 14. The vent 7 and septum 9 are formed to limit contamination within the separation chamber 14. In this regard, vent 7 and septum 9 may be one-way valves. Vent 7 may also be an opening covered by filter material having a porosity designed to allow for air flow but to prevent contamination of the separation chamber 14.

Separation chamber 14 includes a single outlet extending out from end 13. This outlet is seen as tubing 24. Tubing 24 connects to the most tapered end of tapered portion 15, and is mounted thereto and integrally formed with end 13. The combination of the tapered portion 15 and tubing 24 defines a funnel like structure to direct fluid out of the separation chamber 14. The tapering of the outlet in this manner minimizes the potential that fluid will remain within the separation chamber 14. This fluid tubing 24 is dimensioned to control the rate of flow out of the separation chamber 14. Typically, fluid tubing 24 will have an internal diameter of from about twenty thousandths of an inch to about sixty thousandths of an inch.

As seen in FIG. 1, tubing 24 is formed with a Y-section, seen generally at 26. This Y-section 26 includes two arms 28 and 30. One arm 28 will be used to expel waste fluid, i.e. the physiologic fluid and any washing fluid. The other arm 30 will be used to direct the resulting composition of the antibody component, or antigen component/antibody component complex in the eluting solution into an appropriate container, not shown.

In order to facilitate the directing of the fluid from the separation chamber 14 through the appropriate arms 28 and 30 of the tubing 24 a two-way valve 33 is positioned at the Y-intersection. This two-way valve 33 is formed with two separate flow pathways, 29 and 31, through which fluid is selectively directed to either of two arms 28 and 30. Two-way valve 33 is thus operated to direct the flow only through one of these arms, while limiting the possibility of the physiological or washing fluid entering the other such arm.

In place of the two-way valve 33, clamps, not shown, can be positioned at the top of each of the two arms 28 and 30 to prevent unwanted flow. The opening of either of these clamps would then allow for flow down the appropriate one of the two arms 28 and 30. It may also be desirable to position a clamp, seen generally at 39, upstream from the two-way valve 33. This allows the tubing 24 to be temporarily sealed off from the two-way valve 33 during the mixing of the fluids and immunoreactive paramagnetic particles in the separation chamber 14. A filter assembly, not shown, may be disposed in the arm 30. This filter would function to limit the passage of immunoreactive paramagnetic particles or any bacteria present in the physiological fluid. Generally, the filter would be of the type having a pore size of about 0.22 millimicrons.

Assembly 10 (FIG. 1) is typically constructed from a flexible material. As stated above, the container, in which the physiological fluid and immunoreactive paramagnetic particles are placed, is positioned within a magnetic field drawing the immunoreactive paramagnetic particles to one or more sides of the separation chamber 14. This may be accomplished by placing the assembly 10 upon a support containing one or more magnets. In this way the immunoreactive paramagnetic particles would be drawn towards that wall of the separation chamber 14 positioned adjacent the magnets.

Referring to a combination of FIG. 1 and FIGS. 2A and 2B, a preferred embodiment of a support assembly 12 will now be described in detail. Support assembly 12 is formed with a platform 32 upon which the container assembly 10 (FIG. 1) is mounted. This platform 32 includes one or more magnets 34 and a spring biased clasp 36. The magnets 34 are seated in a depression formed in the platform 32 to provide a flat surface upon which the container assembly 10 (FIG. 1) rests. Magnets 34 are preferably a high grade magnetic material prepared from neodymium-iron-boron with a surface field strength sufficient to capture a majority of the immunoreactive paramagnetic particles. In this regard, the magnets 34 should have a sufficient field reach to extend substantially across the separation chamber 14 (FIG. 1). The number of magnets 34 will be dependent upon the size of the container assembly 10 (FIG. 1).

In another embodiment the magnets have been recessed into the platform. The platform has been modified to accept the placement of a stainless steel "keeper" between the disposable chamber and the magnets. The "keeper" is designed to slide in place using a set of grooves milled into the platform. The purpose of the keeper is to shield the chamber from the magnetic field when the chamber and its contents are being mixed. When the magnetic capture of the paramagnetic beads is desired the "keeper" is removed and the chamber is pulled back into a position next to the magnets by the spring biased clasp. The "keeper" can easily be reinserted between the chamber and the magnets when desired.

This magnetic separator is fitted with a variable speed, geared electric motor, geared rotation axle and a belt connecting the two gears. The assembly is designed to accommodate the mixing necessary for sample processing and replaces the previously discussed practice of mixing by placing the chamber on an independent rotator. With the disposable chamber on the separator, the chamber assembly can be rotated end-over-end on the axle with the rotation driven by the electric motor.

This magnetic separator is fitted with an axle that contains a spring biased gear which can be disengaged if desired and will allow the free rotation of the platform and chamber assembly independent of the motor and drive gears. The axle can be reengaged when the platform has been rotated to any desired position. This feature allows the rotation of the chamber and platform from the horizontal to the vertical position and vice versa during the processing steps without the need to turn on the motor. This is particularly helpful when the beads have been captured in the vertical position after the elution solution has been added and the operator desires to reposition the chamber so that the elution solution which drains to the bottom of the chamber can be recovered while the magnetic beads remain captured on the side of the chamber.

The recessed platform is fitted with tubing restraints which allow the free ends of the chamber tubing inlet and outlets to be held during rotation and mixing of the beads with the sample, wash solution or elution.

The above described apparatus leads to the capability to conduct entire operation of mixing, washing, and elution without ever needing to remove the separation chamber from the magnetic separator. The previously disclosed magnetic separator necessitated the removal of the disposable chamber from the magnetic separator for each mixing step and replacement of the chamber on the separator for each magnetic capture step.

The container assembly 10 (FIG. 1) is positioned on the platform 32 (FIG. 2a) to place the separation chamber 14 (FIG. 1) at a location adjacent to magnets 34 (FIG. 2a). This ensures that the magnetic field will pass through substantially all of the separation chamber 14 (FIG. 1).

The container assembly 10 (FIG. 1) is held onto the platform 32 (FIG. 2a) by the spring biased clasp 36. Clasp 36 is formed with two arms 38 and 40 which can be brought into engagement with and hold the separation chamber 14 (FIG. 1) to the platform 32.

This spring biased clasp 36 is designed to releasably grip the container assembly 10 (FIG. 1) about the separation chamber 14 (FIG. 1). This allows the container assembly 10 (FIG. 1) to be repeatedly mounted to and removed from the support assembly 12. This releasable grip is provided by mounting the clasp 36 in such a way to platform 32 so as to be reciprocatively biased in a direction towards platform 32 (FIG. 2a).

For example, spring biased clasp 36 (FIG. 2a) may be mounted to slide along bolts or studs, not shown, extending out from the platform 32. Springs, also not shown, may be positioned about these studs and secured at opposite ends to the platform 32 and the spring biased clasp 36. In this manner the clasp 36 may be pulled outward along the studs but when released retract back to the platform 32.

Platform 32 (FIG. 2a) includes at one end a rest 42. Rest 42 is designed and positioned to engage the tapered portion 15 of end 13 when the container assembly 10 (FIG. 1) is being held onto the platform 32. Further, rest 42 (FIG. 2a) is formed with a cut-away 44 through which tubing 24 extends. The platform 32 is mounted in the support assembly 12 to allow for easy rotation from a vertical to horizontal position.

As illustrated, platform 32 (FIG. 2a) is mounted between two side supports 46 and 48 to an axis 50. Axis 50 is defined by two threaded bolts 51 and 53 each of which is secured at one end to the platform 32 and at the opposite end to one of the side supports 46 or 48. The platform 32 is secured to the individual bolts 51 and 53 to allow for free rotation. Tension is maintained on the platform 32 by mounting springs 52 and 54 between the platform 32 and washer/nut combinations 56 and 58. These washer/nut combinations 56 and 58 are threadably mounted along the bolts 51 and 53 to ensure that the respective springs 52 and 54 remain under tension. This tension ensures that the platform 32 will remain in any desired position about the axis of rotation.

The apparatus 10 (FIG. 1) is operated by first introducing the specific physiological fluid into the separation chamber 14 (FIG. 1) through the fluid tube 16. The desired quantity of immunoreactive paramagnetic particles is then added to the fluid through the septum 9. The fluid tubes 16 and 18 and tubing 24 are closed off by the clamps 20 and 22, and valve 33, respectively.

At this point the container assembly 10 (FIG. 1) need not be positioned on the support assembly 12 (FIG. 2a), and in order to perform the mixing step should not be in position adjacent the magnets 34. The container assembly 10 (FIG. 1) is agitated to thoroughly mix the fluid and immunoreactive paramagnetic particles.

The container assembly 10 (FIG. 1) is then placed on the support assembly 12 (FIG. 2a) with the separation chamber 14 (FIG. 1) placed adjacent to the magnets 34

(FIG. 2a). The magnetic field draws and holds the immunoreactive paramagnetic particles to that side of the separation chamber 14 (FIG. 1) closest to the magnets 34 (FIG. 2a). Valve 33 is operated to release the fluid in the separation chamber 14 (FIG. 1) down through the arm 28.

A washing fluid, i.e. saline, is then introduced into the separation chamber 14 (FIG. 1) through line 18 after the valve 33 (FIG. 1) is closed. Again, the container assembly 10 (FIG. 1) is removed from the support assembly 12 (FIG. 2a), or otherwise the magnetic filed is removed from influencing the immunoreactive paramagnetic particles in the separation chamber 14 (FIG. 1). After sufficiently mixing the washing fluid and immunoreactive paramagnetic particles, the container assembly 10 (FIG. 1) is repositioned on the support assembly 12 (FIG. 2a). The magnetic field of the magnets 34 (FIG. 2a) again draws and holds the immunoreactive paramagnetic particles against a wall of the separation chamber 14 (FIG. 1). The valve 33 (FIG. 1) is opened to release the washing fluid through arm 28.

During the release of both the physiological and washing fluids the container assembly 10 (FIG. 1) is held in the vertical position to allow for a gravity flow of the fluid out of the separation chamber 14 (FIG. 1). After the separation chamber 14 is emptied of the washing fluid, a small quantity of elution fluid is introduced into the separation chamber 14 via the septum 9. The precise amount of elution fluid should be equivalent to the desired amount of the final amount pharmaceutical composition sought. Typically from about 0.1 milliters to about 5 milliters of the elution fluid will be used.

Since only a small quantity of the elution solution is to be used, the container assembly 10 (FIG. 1) may be oriented to expose the fluid to all of the particles, typically by laying the container in a horizontal position. Alternatively, the elution solution is added to the chamber and mixed end-over-end. The elution solution and particles may also be mixed together by removing the container assembly 10 (FIG. 1) from the support assembly 12 (FIG. 2a), and thereby removing the magnetic field. This allows the elution solution to bathe all of the immunoreactive paramagnetic particles and thus act upon the antigen component/antibody component complex for the purpose of releasing the antibody component or the entire complex.

After a sufficient amount of time the container assembly 10 (FIG. 1) is again placed in the vertical position, by rotating the support assembly 12 (FIG. 2a) and the valve 33 (FIG. 1) is opened to release the final product through the arm 30. This product is collected and usually neutralized by the addition of a suitable neutralizing agent.

A single use kit for performing the described method will now be discussed with reference to FIG. 3. FIG. 3 shows a schematic diagram of the present invention in the kit format. Step 1 of this method involves adding a sufficient amount of a patient's physiological fluid and a sufficient amount of allergen coated paramagnetic particles to bind a predetermined amount of allergen specific antibody to container assembly 10 (FIG. 1), that generally includes chamber 14 (FIG. 1) having multiple inlets and outlets.

In step 2 of the method the physiological fluid and allergen coated paramagnetic particles are incubated for a sufficient period of time to bind the allergen-specific antibody to the allergen in the separation chamber. In step 2 the allergen-specific antibody bound to the allergen coated paramagnetic particles are separated from unbound fluid. In step 4 a wash solution is added to the container assembly through an inlet port. The wash solution is a physiological saline solution. In step 5 an amount of physiologically acceptable elution solution is added to elute the allergen-specific antibody from the allergen coated paramagnetic particles, but less than an amount of the elution solution to require concentration of the recovered allergen-specific antibody.

The allergen-specific antibody is separated from the retained allergen coated paramagnetic particles and withdrawn through a filter. The eluted antibody solution is withdrawn using a syringe. The syringe is fitted with a filter and the eluted antibody solution is injected into a vial of neutralizing solution. In step 7 the allergen-specific antibody is added to a physiologically acceptable neutralizing solution to obtain a solution having a physiologically acceptable pH, but less than an amount of said neutralizing solution to require concentration on of the recovered allergen-specific antibody. In step 8 the allergen-specific antibody is combined with the patient's allergen and the complex is shipped to the allergist to treat allergy by immunization with autologous antigen antibody immune complexes.

The following examples demonstrate the effectiveness of the described method and apparatus in recovering anti-factor VIII antibody (Inhibitor) from a physiological fluid. The beads used in these examples were prepared with factor VIII covalently bound to their surface. This first involved covalently binding an epoxy moiety to the surface of each bead by treating uncoated beads, sold under the identification number M450 by the Dynal Company of Great Neck, N.Y., with epichlorohydrin. These beads were then treated with 1,6,-hexanediamine to yield beads with primary amino groups. Factor VIII carbohydrate residues were oxidized with sodium periodate to yield aldehyde groups which were then reacted with the amine derivatized beads to form reversible Schiff's based between the amino and aldehydes groups. These Schiff's bases were reduced with sodium cyanoborohydride to form permanent covalent bonds between the residues of the amino and aldehyde groups. These beads were used in the following two experiments to demonstrate the ability of the factor VIII-beads to bind anti-factor VIII antibody (inhibitor) from solution.

In lieu of using plasma for these experiments a comparable physiological solution was prepared which consisted of 50 mg/mL of a commercially available human serum albumin (HSA) and 10 mg/mL of a commercially available human IgG, both of which are by the Hyland Division of Baxter Healthcare Corporation of Deerfield, Ill., in phosphate buffered saline, which approximated the total protein content of plasma. Radiolabeled anti-factor VIII was added to the HSA and IgG solution at a concentration of 1.0 μg/mL for each experiment.

The procedures followed for each experiment were as follows:

1. Add solution containing $^{125}I$-labeled factor VIII inhibitor at 1 μg/mL to the chamber.
2. Add factor VIII bearing bead suspension to the chamber through the septum port using a syringe and hypodermic needle. The number of beads per experiment is listed in Table 1 below.
3. Incubate the beads and plasma with end-over-end mixing for 1 hour. The beads must be mixed at least occasionally or the will settle to the bottom of the chamber.

4. Capture beads after the incubation step by placing the chamber on the magnetic separator, i.e. placing the container assembly on the support assembly in close proximity to the magnets, in the vertical position. Drain the plasma or blood from the chamber to a waste container.
5. Fill the chamber with approximately 40 mm of normal saline wash solution and resuspend the beads by mixing briefly.
6. Recapture beads and drain the saline wash solution from the chamber to waste.
7. Repeat steps 5 and 6 above.
8. Add 2.0 mL of 0.1 M glycine elution buffer, pH 2.5, to the chamber, resuspend the beads and mix for 10 minutes.
9. Capture the beads by placing the support assembly in the horizontal position and repositioning the chamber in the separator clamps. Accomplishing the bead capture in the horizontal position prevents the beads and elution buffer from draining to the bottom of the chamber while attempting to place the chamber on the separator in the vertical position.
10. Rotate the separator and chamber into the vertical position and allow the elution buffer to drain to the bottom of the chamber.
11. Repeat steps 8 through 10.
12. Quantitate the factor VIII inhibitor recovered in the elution buffer.
13. Results from the two large scale experiments using factor VIII-beads for the removal of anti-factor VIII are summarized in Table 1.

TABLE 1

| SUMMARY OF THE LARGE SCALE EXPERIMENTS[1,2] | | |
|---|---|---|
| | Experiment Number 1 | Experiment Number 2 |
| Number of beads | ($1 \times 10^9$ Beads) | ($2 \times 10^9$ Beads) |
| Factor VIII inhibitor | | |
| Total bound to beads | 13.25 ug | 22.57 ug |
| Total recovered | 3.22 ug | 11.65 ug |
| % Recovered | 24% | 52% |
| In 1st Elution | 3.02 ug (94%) | 11.10 ug (95%) |
| In 2nd Elution | 0.20 ug (6%) | 0.55 ug (5%) |

[1]both experiments were conducted under the following conditions:
45 ml volume processed
50 mg/mL HSA &
10 mg/mL human IgG
1.0 ug/mL mouse $^{125}$I-anti FVIII
elution with 2.0 mL of 0.1 M glycine, pH 2.5
[2]The recovery concentration of the $^{125}$I anti-factor VIII, that is the factor VIII inhibitor during each step of the experiment, that is the $^{125}$I factor VIII inhibitor recovery on the beads as well as at each elution step was quantified by using a gamma counter to count the gamma activity at each level of recovery, which was divided by the total gamma activity of the $^{125}$I factor VIII inhibitor in the initial amount used in each experiment.

The large scale experiments using factor VIII-Deeds to remove $^{125}$I-labeled Hyland anti-factor VIII, that is factor VIII inhibitor, from solution demonstrated the capability of the system and apparatus.

Assessment of Antigen Binding Function of Recovered Anti-Factor VIII Antibodies (Inhibitor)

A series of experiments were conducted to evaluate the antigen binding function of the recovered $^{125}$I factor VIII inhibitor. These experiments were conducted using factor VIII beads and $^{125}$I- labeled Hyland monoclonal anti-factor VIII antibody. Factor VIII beads were incubated with 1 μg/mL of the above recovered $^{125}$I factor VIII inhibitor in a 50 mg/mL human serum albumin and 10 mg/mL human IgG solution for 1 hour. The beads were then washed twice with normal saline and the $^{125}$I factor VIII inhibitor was subsequently eluted with 0.1 M glycine, pH 2.5. The elution solution containing the recovered $^{125}$I factor VIII inhibitor was then neutralized with a suitable buffer and incubated with a second identical aliquot of factor VIII bearing beads for 2 hour. The beads were washed twice with saline and the amount of bound factor VIII antibodies was determined in a similar manner as described above using the gamma activity of the recovered $^{125}$I factor VIII inhibitor in comparison to the gamma activity of the initial amount of $^{125}$I factor VIII inhibitor.

Utilization of a second aliquot of factor VIII beads as the target for binding of the recovered factor VIII antibodies made the quantitation of bound factor VIII antibodies much more reliable than trying to measure the factor VIII: factor VIII antibodies complexes in solution. Use of the target factor VIII beads also makes this a "worst case" measurement since the kinetics of the factor VIII antibodies binding to a solid phase bead are less favorable binding of factor VIII antibodies to soluble factor VIII. The results confirm the retention of excellent antigen binding capacity of the recovered antibody. This function is essential to the formation of the factor VIII inhibitor: factor VIII immune complexes subsequently used in patient immunization. Binding of the anti-factor VIII was also demonstrated to be dependent on the number of beads used which is consistent with the stated kinetic limitations of this model. The data for this experiment is summarized in Table 2.

TABLE 2

Summary of the Test Experiments on Rebinding Recovered Factor VIII Inhibitor[12]

| | Experiment Number 1 | Experiment Number 2 |
|---|---|---|
| Number of Beads | ($4 \times 10^7$ Beads) | ($8 \times 10^7$ Beads) |
| ANTI-FVIII | | |
| Total % bound to bead aliquot 1 | 24.0 | 34.8 |
| Total % eluted in glycine washes | 83.2 | 84.8 |
| Total % bound of amount offered to bead aliquot 2 | 77.0 | 88.2 |

[1]These experiments were conducted under the following conditions:
2 mL volume processed
50 mg/mL HSA &
10 mg/mL human IgG
1.0 ug/mL mouse 125I-anti FVIII
elution with 100 uL of 0.1 M glycine, pH 2.5
bead aliquots 1 & 2 for each experiment were of the same size
[2]Average of triplicate samples The following examples demonstrate the effectiveness of the described method and apparatus for the recovery of anti-ragweed antibodies from the plasma of subjects known to be allergic to ragweed allergen extracts. The beads used in this demonstration were prepared by the following:

1. Uncoated Dynal M-450 beads were purchased from Dynal. Great Neck, N.Y. and modified by the use of epichlorohydrin to have covalently attached epoxy residues on their surface.

2. The epoxy derivatized beads were modified by the addition of 1,6,-hexanediamine to yield beads with a primary amine group on their surface.

3. The amine beads were then mixed with ragweed allergen and 1-ethyl-3-(3-dimethylaminopropyl)-carbodiimide to facilitate the covalent coupling of ragweed allergen to the amine groups on the surface of the beads, The procedure is generally the same as previously described, except that the ragweed allergen coated beads were substituted for the Factor VIII beads and subject plasma was used in the chamber instead of the comparable physiological solution of 50 mg/mL of human serum albumin and 10 mg/mL of human IgG used in the Factor VIII example. Additionally, only a single glycine (0.2M glycine buffer, pH 2.1) elution step was utilized in this experiment. Two mL of glycine was added.

The elution buffer was neutralized by the addition of solid Tris buffer.

The amount of IgG anti-ragweed antibody present in the neutralized elution was quantitated by using an enzyme-linked immunosorbent assay (ELISA) for the detection of anti-ragweed IgG. Approximately 0.5 $\mu$g of IgG anti-ragweed was recovered using $2 \times 10^9$ ragweed allergen coated beads and 40 mL of subject plasma.

The capacity of the recovered anti-ragweed antibodies to form immune complexes is also demonstrated by the fact that the antibody is capable of binding to the ragweed allergen coated wells used in the ELISA for the detection of IgG antibodies. The specificity of the anti-ragweed antibodies can be demonstrated by competitive binding inhibition assays which also demonstrate the ability of the recovered anti-ragweed antibody to bind to ragweed allergens.

While the preferred embodiments have been described, various modifications and substitutions may be made thereto without departing from the scope of the invention. Accordingly, it is to be understood that the invention has been described by way of illustration and not-limitation.

We claim:

1. A magnetic separator apparatus comprising:
   a housing defining a chamber, which includes at least a first inlet and at least a first outlet for gaining entrance to the chamber;
   a support platform to which the housing is releasably mounted, the support platform including one or more magnets located at a surface of the support platform against which the housing is releasably mounted;
   a base having at least two spaced apart portions between which the support platform is positioned;
   one or more arms selectively connected at one location to the support platform and at a second location to one of the base portions, with one of such connections of each of the one or more arms being by means allowing for rotation of the support platform about an axis defined by the arms; and
   spring biased means associated with the one or more arms to hold the support platform at a location about the axis of rotation.

2. The apparatus of claim 1 wherein the one or more arms are at least a single shaft connected at one point to the support platform and at another point to the base, with one of the points of connection being freely rotatable about an axis defined by the shaft.

3. The apparatus of claim 1 wherein the base includes two spatially separated beams between which the support platform is positioned, with the one or more arms being first and second shafts connected at one location to the support platform and at another location to a respective one of the beams, wherein each of the first and second shafts is mounted at one of the locations for free rotation about an axis defined by the shaft.

4. The apparatus of claim 1 wherein the base includes two spatially separated beams between which the support platform is positioned, with the one or more arms being first and second shafts connected at one location to the support platform and at another location to a respective one of the beams, wherein each of the first and second shafts is mounted at one of the locations for free rotation about an axis defined by the shaft and wherein the spring biased means is first and second springs mounted respectively about the first and second shafts, wherein each of the first and second springs remains under tension to bear against the support platform.

5. The apparatus of claim 4 wherein the housing is a cylindrical container tapered at one end, with the tapering end in fluid communication with a single outlet.

6. The apparatus of claim 5 wherein the single outlet includes a two-way valve selectively communicating with first and second fluid pathways.

7. The apparatus of claim 1 wherein the support platform includes a spring biased clip which includes a portion to bear against and hold the housing to the support platform, the clip being resiliently biased in a first direction towards the support platform, while being moveable in a second direction away from the support platform to allow placement of the housing between the clip portion and the support platform.

8. The apparatus of claim 6 wherein platform includes a spring biased clip which includes a portion to bear against and hold the housing to the support platform, the clip being resiliently biased in a first direction towards the support platform, while being moveable in a second direction away from the support platform to allow placement of the housing between the clip portion and the support platform.

9. A magnetic separator comprising:
   a support platform to which a housing is releasably mounted, the support platform including one or more magnets located at a surface of the support platform against which the housing is releasably mounted;
   a base having at least two spaced apart portions between which the support platform is positioned;
   one or more arms selectively connected at one location to the support platform and at a second location to one of the base portions, with one of such connections of each of the one or more arms being by means allowing for rotation of the support platform about an axis defined by the arms.

10. A magnetic separator comprising:
    a support platform to which a housing is releasably mounted, the support platform including one or more magnets located at a surface of the support platform against which the housing is releasably mounted;
    a base having at least two spaced apart portions between which the support platform is positioned;
    one or more arms selectively connected at one location to the support platform and at a second location to one of the base portions, with one of such connections of each of the one or more arms being by means allowing for rotation of the support platform about an axis defined by the arms; and
    spring biased means associated with the one or more arms to hold the support platform at a location about the axis of rotation.

11. The separator of claim 10 wherein the one or more arms are at least a single shaft connected at one point to the support platform and at another point to the base, with one of the points of connection being freely rotatable about an axis defined by the shaft.

12. The separator of claim 10 wherein the base includes two spatially separated beams between which the support platform is positioned, with the one or more arms being first and second shafts connected at one location to the support platform and at another location to a respective one of the beams, wherein each of the first and second shafts is mounted at one of the locations for free rotation about an axis defined by the shaft.

13. The separator of claim 12 wherein the spring biased means is first and second springs mounted respectively about the first and second shafts, wherein each of the first and second springs remains under tension to bear against the support platform.

14. The separator of claim 10 wherein the support platform includes a spring biased clip which includes a portion to bear against and hold the housing to the support platform, the clip being resiliently biased in a first direction towards the support platform, while being moveable in a second direction away from the support platform to allow placement of the housing between the clip portion and the support platform.

15. The separator of claim 13 wherein the support platform includes a spring biased clip which includes a portion to bear against and hold the housing to the support platform, the clip being resiliently biased in a first direction towards the support platform, while being moveable in a second direction away from the support platform to allow placement of the housing between the clip portion and the support platform.

16. A method of preparing a pharmaceutical composition of a specific target antibody component population in a pharmaceutically acceptable carrier from a physiological fluid using paramagnetic particles bearing an antigen component selective for the target antibody component population in combination with the magnetic system of claim 1 comprising:
   supplying a quantity of the paramagnetic particles to the housing chamber;
   introducing the physiological fluid into the housing chamber; mixing the paramagnetic particles and the physiological fluid; removing the physiological fluid from the housing chamber;
   washing the housing chamber with an acceptable wash fluid;
   draining the wash fluid from the housing chamber;
   providing the housing chamber with a pharmaceutically acceptable eluting solution;
   mixing the paramagnetic particles and eluting solution; and
   removing the eluting solution from the housing chamber.

17. A method of preparing a pharmaceutical composition of a specific target antibody component population in a pharmaceutically acceptable carrier from a physiological fluid using paramagnetic particles bearing an antigen component selective for the target antibody component population in combination with the magnetic system of claim 4 comprising:
   supplying a quantity of the paramagnetic particles to the housing chamber;
   introducing the physiological fluid into the housing chamber; mixing the paramagnetic particles and the physiological fluid to form an antigen component and antibody component complex; removing the physiological fluid from the housing chamber;
   washing the housing chamber with an acceptable wash fluid;
   draining the wash fluid from the housing chamber;
   providing the housing chamber with a pharmaceutically acceptable eluting solution;
   mixing the paramagnetic particles and eluting solution; and
   removing the eluting solution from the housing chamber.

18. The method of claim 17 further including a step of orientating the housing chamber in a substantially horizontal orientation prior to the steps of removing the physiological fluid and removing the eluting solution.

19. The method of claim 17 further including the step of neutralizing the eluting solution after removal from the housing chamber.

20. The method of claim 17 wherein the selected eluting solution is of the type to cause said antigen component and antibody component complex to cleave from said paramagnetic particles.

21. The method of claim 17 wherein the selected eluting solution is of the type to cause said antibody component to cleave from the antigen component bound to the paramagnetic particles.

22. The method of claim 17 wherein the first and second steps of mixing are performed by first removing the housing chamber from the support platform and second by shaking the housing chamber to admix the paramagnetic particles and the respective solutions, and subsequently affixing the housing chamber to the support platform.

23. The method of claim 17 wherein the first and second steps of mixing are performed by rotating the support platform with the housing chamber supported thereon.

* * * * *